United States Patent [19]

Higuchi et al.

[11] Patent Number: 5,087,736

[45] Date of Patent: * Feb. 11, 1992

[54] PROCESS FOR PRODUCING METHYL METHACRYLATE

[75] Inventors: Hirofumi Higuchi; Koichi Kida, both of Niigata, Japan

[73] Assignee: Mitsubishi Gas Chemical Company, Inc., Tokyo, Japan

[*] Notice: The portion of the term of this patent subsequent to Feb. 11, 2009 has been disclaimed.

[21] Appl. No.: 530,089

[22] Filed: May 29, 1990

[30] Foreign Application Priority Data

Jul. 14, 1989 [JP] Japan .................................. 1-180558

[51] Int. Cl.$^5$ ............................................ C07C 67/20
[52] U.S. Cl. .................................. 560/215; 560/211; 560/205
[58] Field of Search .......................... 560/215, 211

[56] References Cited

FOREIGN PATENT DOCUMENTS 60-78939 5/1985 Japan .

Primary Examiner—Paul J. Killos

Attorney, Agent, or Firm—Frishauf, Holtz, Goodman & Woodward

[57] ABSTRACT

Disclosed is a process for producing methyl methacrylate which comprises:

(I) a step of reacting acetone and prussic acid to form acetonecyanhydrin;

(II) a step of hydrating the acetonecyanhydrin obtained in the step (I) to form α-hydroxyisobutyric acid amide;

(III) a step of reacting the α-hydroxyisobutyric acid amide obtained in the step (II) which methyl formate to form methyl α-hydroxyisobutyrate and formamide;

(IV) a step of dehydrating the methyl α-hydroxyisobutyrate obtained in the step (III) to form methyl methancrylate; and (V) a step of decomposing the formamide obtained in the step (IV) into ammonia and carbon monoxide.

The process can produce methyl methacrylate at high yields without by-production of acidic ammonium sulfate.

15 Claims, No Drawings

PROCESS FOR PRODUCING METHYL METHACRYLATE

BACKGROUND OF THE INVENTION

1. Field of the Invention

The present invention relates to a process for producing methyl methacrylate from acetone and methyl formate, or from acetone, methanol and carbon monoxide as starting materials.

A large amount of methyl methacrylate is used as a starting material for production of various polymers, and the methyl methacrylate is a greatly important intermediate in industrial use.

2. Description of Related Arts

A process for producing methyl methacrylate in which acetonecyanhydrin is prepared from acetone and prussic acid, α-hydroxyisobutyric acid amide is prepared from the acetonecyanhydrin in the presence of sulfuric acid, and then methyl methacrylate is prepared using methacrylamide derived from the α-hydroxyisobutyric acid amide is well known, as described in, for example, Kirk Othmer "Encyclopedia of Chemical Technology", 3rd ed., Vol. 15, p. 357. This process is widely carried out on a commercial scale.

The conventional process, however, has disadvantages in that large amounts of waste sulfuric acid and acidic ammonium sulfate are by-produced and the treatment thereof increases production costs of methyl methacrylate.

Heretofore, the acidic ammonium sulfate has been converted into ammonium sulfate as a fertilizer by addition of ammonia. Presently, however, a demand for the ammonium sulfate fertilizer is limited. For this reason, in recent years, a method of recovering sulfuric acid by decomposition of acidic ammonium sulfate has been put to practical use. This method, however, increases production costs and furthermore, since the nitrogen is insufficiently recovered, it is not a very economical process.

In order to overcome the problems as described above, the present inventors have proposed a method of preparation of methyl methacrylate without use of sulfuric acid according to the route shown by the reaction equation (I), in Japanese Patent Application Laid-Open No. 78939/1985.

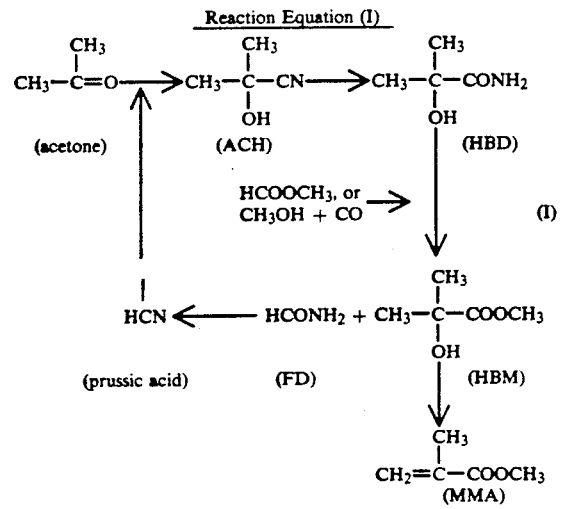

In the above equation, ACH represents acetonecyanhydrin; HBD, α-hydroxyisobutyric acid amide; HBM, methyl α-hydroxyisobutyrate; FD, formamide; and MMA, methyl methacrylate (same also in the equation (II)).

SUMMARY OF THE INVENTION

The present invention is intended to improve the method disclosed in Japanese Patent Application Laid-Open No. 78939/1985.

An object of the present invention is to provide a process for producing methyl methacrylate without use of sulfuric acid. Another object of the present invention is to provide a process for producing methyl methacrylate at a high yield without acidic ammonium sulfate resulting as a by-product.

The present invention relates to a process for producing methyl methacrylate according to the route shown by the reaction equation (II).

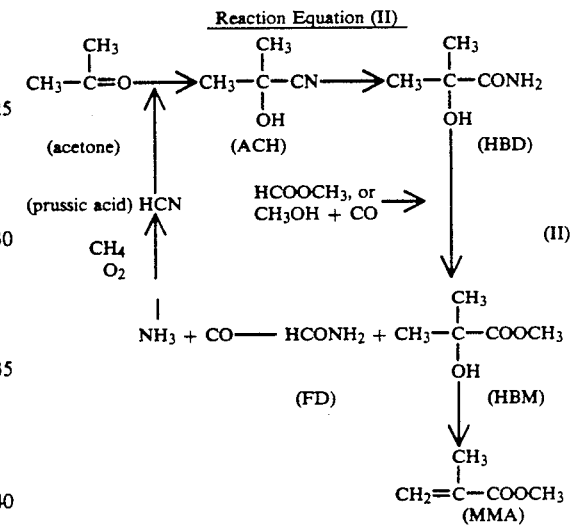

That is, the present invention provides a process for producing methyl methacrylate which comprises:

(I) a step of reacting acetone and prussic acid to form acetonecyanhydrin;

(II) a step of hydrating the acetocyanhydrin obtained in the step (I) to form α-hydroxyisobutyric acid amide;

(III) a step of reacting the α-hydroxyisobutyric acid amide obtained in the step (II) with methyl formate, or with methanol and carbon monoxide to form methyl α-hydroxyisobutyrate and formamide;

(IV) a step of dehydrating the methyl α-hydroxyisobutyrate obtained in the step (III) to form methyl methacrylate; and (V) a step of decomposing the formamide obtained in the step (IV) into ammonia and carbon monoxide.

DESCRIPTION OF PREFERRED EMBODIMENTS

More specifically, the present invention provides a process for producing methyl methacrylate without use of sulfuric acid, in place of the conventional method in which prussic acid and acetone are used as starting materials and sulfuric acid is used. In accordance with the process of the present invention, as illustrated in the reaction equation (II), formamide is formed in place of acidic ammonium sulfate by-produced in the conventional method, and then decomposed into ammonia and carbon monoxide. These ammonia and carbon monoxide are recovered and converted into prussic acid and methyl formate, for example, respectively, which are then recycled to the reaction system for reuse.

In the method disclosed in Japanese Patent Application Laid-Open No. 78939/1985, as illustrated in the reaction equation (I), formamide formed is dehydrated into prussic acid, and this prussic acid is recycled to the reaction system.

In accordance with the process of the present invention, as illustrated in the reaction equation (II), formamide formed is decomposed into ammonia and carbon monoxide for reuse.

The ammonia thus recovered is converted into prussic acid by utilizing the conventional apparatus for production of prussic acid as such, which acid is then recycled to the reaction system. Namely, in the conventional apparatus for industrial production of prussic acid, prussic acid is synthesized, for example, from ammonia, methane and air by the Andrussow method.

Carbon monoxide as recovered herein can be recycled as such into the reaction system along with methanol, or after conversion into methyl formate by reacting with methanol, the resulting methyl formate can be recycled to the reaction system.

In the process of the present invention, as described above, there is no by-production of acidic ammonium sulfate which is a weak point of the conventional process for production of methyl methacrylate by the acetonecyanhydrin method, and nitrogen of high value is recovered as ammonia and reused. Thus the process of the present invention has high industrial significance.

The process of the present invention will hereinafter be explained in detail.

First, the synthesis of acetonecyanhydrin by reaction of prussic acid and acetone is carried out by the known method. This reaction is carried out in the presence of an alkali catalyst at a molar ratio of acetone to prussic acid of 0.95:1 to 1.5:1 at a reaction temperature ranging between 0° and 30° C. to obtain acetonecyanhydrin with high selectivity.

Then, α-hydroxyisobutyric acid amide is synthesized by a hydration reaction of the acetonecyanhydrin. This hydration reaction is carried out by the use of a solid catalyst containing manganese as a main component in the presence of an excessive amount of water, and more preferably combined with a hydrophilic solvent such as acetone or methanol at a reaction temperature of 30° to 90° C. in a liquid phase. In this reaction, acetonecyanhydrin is converted into α-hydroxyisobutyric acid amide with high selectivity. When acetone is used as a reaction solvent, there is an advantage that the reaction solution obtained at the step of synthesis of acetonecyanhydrin can be utilized as an acetonecyanhydrin starting material in the present reaction without separation of unreacted acetone.

When water and the solvent, etc. are distilled away from the hydration reaction solution by the usual method, α-hydroxyisobutyric acid amide is obtained.

Then, methyl formate and, if necessary, methanol are added to α-hydroxyisobutyric acid amide to dissolve it and, thereafter, an amide-ester exchange reaction is carried out. Although the reaction proceeds both in the absence of a catalyst and in the presence of an alumina catalyst, for example, at elevated temperatures, it is preferably carried out under mild condition of not more than 120° C. and in a substantially anhydrous state by the use of alkali metal or alkaline earth metal alcolate or their metal oxides as a catalyst.

Representative examples of catalysts to be used in the reaction are sodium methylate, calcium methylate, sodium oxide, and calcium oxide. Alkali metal or alkaline earth metal can be added to the reaction system as such, because the reaction system contains methanol and thus the alkali metal or alkaline earth metal is converted into the corresponding metal alcolate.

In this amide-ester exchange reaction, it is preferred that an excess amount of methyl formate relative to α-hydroxyisobutyric acid amide is used, and the reaction is carried out in a temperature range of 20° to 120° C. Under these conditions, the reaction reaches an equilibrium state in a residence time of 15 minutes to 10 hours, and methyl α-hydroxyisobutyrate and formamide are prepared with high selectivity.

By distillation of the reaction solution at the amide-ester exchange step, unreacted methyl formate and α-hydroxyisobutyric acid amide, formed methyl α-hydroxyisobutyrate and formamide, and the catalyst are separated and recovered. The methyl α-hydroxyisobutyrate and formamide thus recovered are introduced to a dehydration step and a decomposition step, respectively, as described hereafter. The unreacted starting materials recovered are returned to the reaction system and reused.

In the amide-ester exchange step, even if carbon monoxide and methanol are used in place of methyl formate, the desired reaction proceeds with high yields. Also, in the case of using carbon monoxide and methanol, the reaction is carried out by the use of the same catalyst as described above, and it is preferred that the reaction is carried out in the aforementioned temperature range and at a carbon monoxide pressure of 10 to 150 kg/cm$^2$G.

In the case that methyl formate is used as a starting material and the reaction is carried out with methanol as a solvent, it is preferred that carbon monoxide is introduced and the reaction is carried out under pressure. This facilitates a high conversion of α-hydroxyisobutyric acid amide.

The dehydration reaction of methyl α-hydroxyisobutyrate is carried out either in a liquid phase or in a gas phase. In order to obtain methyl methacrylate in a high yield, it is preferred that the reaction is carried out in a gas phase.

In the gas phase reaction, a solid acid catalyst having an acidic site is preferably used. For example, silica, alumina, silica-alumina, zeolite, natural clay minerals, and those obtained by adjusting the degree of acid of the above compounds with phosphoric acid, phosphoric acid salts or an alkali solution are used.

The dehydration reaction is carried out by dehydrating vaporized methyl α-hydroxyisobutyrate singly or in the presence of methanol, or a small amount of a diluting agent such as steam or inert gas at a reaction temperature of 200° to 400° C. The use of methanol is effective to prevent by-production of methacrylic acid.

The methyl methacrylate thus formed is purified by extraction and distillation, resulting in a high purity methyl methacrylate.

In addition, the formamide recovered at the above amide-ester exchange step is easily decomposed into ammonia and carbon monoxide by the method as described below.

The decomposition reaction is carried out by heating formamide in the absence of a catalyst or in the presence of a basic catalyst and in a gas phase or a liquid phase. In order to prevent by-production of prussic acid, it is preferred that the reaction is carried out at a temperature of not more than 300° C.

As the catalyst, active carbon, sodium hydroxide, sodium cyanide, metal alcolate or calcium oxide, for example, is effectively used.

Preferably, formamide is dehydrated in a liquid phase in the presence of a catalyst at a temperature of 120° to 220° C. with stirring while taking formed gas out of the reaction system. From a mixed gas of ammonia formed and carbon monoxide, ammonia is separated and recovered by cooling under pressure or absorption, and the residue becomes carbon monoxide.

The ammonia thus recovered is again converted into prussic acid by the known method, and recycled to the process of the present invention. For production of prussic acid from recovered ammonia, when methane is used as a starting material, the Andrussow method utilizing ammoxidation and the Degussa method not using oxygen are employed, and when higher alkane is used as a starting material, the Shawinigen method is employed. In addition, by supplying the recovered ammonia into the plant for production of acrylonitrile through ammoxidation of propylene in the Sohio method, prussic acid can be obtained as by-product.

On the other hand, carbon monoxide recovered is, as illustrated by the reaction equation (II), supplied as such to the amide-ester exchange step along with methanol, or after conversion into methyl formate through reaction with methanol, supplied to the amide-ester exchange step.

In accordance with the process of the present invention, methyl methacrylate can be produced with high yields from acetone and methyl formate, or from acetone, methanol and carbon monoxide as starting materials without by-production of acidic ammonium sulfate as in the conventional methods.

The present invention is described in greater detail with reference to the following examples.

Example 1

151 g of acetone and 2 g of an anionic exchange resin catalyst were placed in a 300-milliliter four-necked round flask equipped with a stirrer, and maintained at 5° C. on a cooling bath. Then, 54 g of prussic acid was added therein by a dropping funnel in small portions while stirring in such a manner that the liquid temperature did not exceed 10° C. After completion of this addition, the liquid temperature was raised to 10° C., and stirring was further continued for 15 minutes to complete the reaction.

An HPLC analysis of the reaction product solution showed that the conversion of prussic acid was 100%, and the yield of acetonecyanhydrin was 99.5%. After separation of the anionic exchange resin catalyst from the product solution by filtration, 182 g of water was added to prepare 387 g of a feed solution for the hydration reaction.

This feed solution was supplied by a quantitative pump at a rate of 10 g/hr into a glass tubular reactor with an inner diameter of 10 mm, packed with 10 g of a 20 to 30 mesh δ-MnO$_2$ catalyst and soaked in a bath maintained at 60° C.

After the reaction for 10 hours, the reaction product solution was analyzed by HPLC. This analysis showed that the conversion of acetonecyanhydrin was 87% and the yield of α-hydroxyisobutyric acid amide was 81%. By-products were acetone and formamide.

From this reaction solution, purified α-hydroxyisobutyric acid amide was obtained by distillation and crystallization.

155 g of the purified α-hydroxyisobutyric acid amide, 150 g of methanol, 180 g of methyl formate, and 5 g of a 28% methanol solution of sodium methylate as a catalyst were placed in a 800-milliliter jacketed flask equipped with a stirrer, and reacted at a temperature of 50° C. for 5 hours.

The reaction solution thus obtained was analyzed by GC. This GC analysis showed that the conversion of α-hydroxyisobutyric acid amide was 65%, the yield of methyl α-hydroxyisobutyrate was 64%, and the yield of formamide was 64%.

From this reaction solution, purified methyl α-hydroxyisobutyrate and purified formamide were obtained by distillation.

To 118 g of the above purified methyl α-hydroxyisobutyrate was added 118 g of methanol to prepare a feed solution. This feed solution was supplied by a quantitative pump at a rate of 3 g/hr into a Pyrex glass tubular reactor with an inner diameter of 100 mm, packed with 5 g of Molecular Sieve 13X. This feed solution was distilled by heating and then introduced into the catalyst layer and reacted at a temperature of 250° C.

At a point that the reaction was carried out for 5 hours, the reaction solution was analyzed by GC. This GC analysis showed that the conversion of methyl α-hydroxyisobutyrate was 98%, and the yield of methyl methacrylate was 90%.

All the reaction solution was extracted with water to remove methanol, and then purified to obtain 65 g of methyl methacrylate.

Separately, 180 g of purified formamide and 1 g of a calcium oxide catalyst were placed in a 300-milliliter four-necked round flask equipped with a stirrer and a reflux condenser, and heated to 150° C. with a mantle heater while stirring.

Generated gas mist produced was dropped with a Brine reflux condenser. Ammonia gas was absorbed in a trap containing an aqueous sulfuric acid solution and measured by neutralization titration. Carbon monoxide gas was measured with a gas meter and analyzed by GC.

The yield of ammonia was 94%, and the yield of carbon monoxide was 89%.

What is claimed is:

1. A process for producing methyl methacrylate which comprises:
   (I) a step of reacting acetone and prussic acid to form acetonecyanhydrin;
   (II) a step of hydrating the acetonecyanhydrin obtained in the step (I) to form α-hydroxyisobutyric acid amide;
   (III) a step of reacting the α-hydroxyisobutyric acid amide obtained in the step (II) with methyl formate to form methyl α-hydroxyisobutyrate and formamide;
   (IV) a step of dehydrating the methyl α-hydroxyisobutyrate obtained in the step (III) to form methyl methacrylate; and
   (V) a step of decomposing the formamide obtained in the step (IV) into ammonia and carbon monoxide.

2. A process for producing methyl methacrylate which comprises:

(I) a step of reacting acetone and prussic acid to form acetonecyanhydrin;

(II) a step of hydrating the acetonecyanhydrin obtained in the step (I) to form α-hydroxyisobutyric acid amide;

(III) a step of reacting the α-hydroxyisobutyric acid amide obtained in the step (II) with methanol and carbon monoxide to form methyl α-hydroxyisobutyrate and formamide;

(IV) a step of dehydrating the methyl α-hydroxyisobutyrate obtained in the step (III) to form methyl methacrylate; and (V) a step of decomposing the formamide obtained in the step (IV) into ammonia and carbon monoxide.

3. The process as claimed in claim 1 or 2, wherein the ammoxidation of methane and air is carried out using the ammonia recovered in the step (V) to form prussic acid, and the prussic acid thus obtained in recycled to the step (I) for reuse.

4. The process as claimed in claim 1 or 2, wherein carbonylation of methanol is carried out using the carbon monoxide obtained in the step (V) to form methyl formate, and the methyl formate thus obtained is recycled to the step (III) for reuse.

5. The process as claimed in claim 1 or 2, wherein the molar ratio of acetone to prussic acid is 0.95:1 to 1.5:1.

6. The process as claimed in claim 1 or 2, wherein the hydration reaction in the step (II) is carried out in the presence of a solid catalyst and in the presence of an excessive amount of water.

7. The process as claimed in claim 6, wherein the solid catalyst contains manganese as a main component.

8. The process as claimed in claim 1 or 2, wherein the reaction in the step (III) is carried out in the presence of methanol.

9. The process as claimed in claim 1 or 2, wherein the reaction in the step (III) is carried out in the presence of a catalyst.

10. The process as claimed in claim 9, wherein the catalyst is sodium methylate, calcium methylate, sodium oxide or calcium oxide.

11. The process as claimed in claim 1 or 2, wherein the dehydration reaction in the step (IV) is carried out in a gas phase.

12. The process as claimed in claim 1 or 2, wherein the dehydration reaction in the step (IV) is carried out in the presence of a solid catalyst.

13. The process as claimed in claim 12, wherein the solid catalyst is silica, alumina, silica-alumina, zeolite or natural clay.

14. The process as claimed in claim 1 or 2, wherein the decomposition reaction in the step (V) is carried out in the presence of a catalyst.

15. The process as claimed in claim 14, wherein the catalyst is active carbon, sodium hydroxide, sodium cyanide, metal alcolate or calcium oxide.

* * * * *